(12) United States Patent
Finitzo et al.

(10) Patent No.: US 7,228,315 B2
(45) Date of Patent: *Jun. 5, 2007

(54) COMPUTER-AUTOMATED IMPLEMENTATION OF USER-DEFINABLE DECISION RULES FOR MEDICAL DIAGNOSTIC OR SCREENING INTERPRETATIONS

(76) Inventors: Terese Finitzo, 3312 Amherst, Dallas, Dallas County, TX (US) 75225; Kenneth D. Pool, Jr., 3401 Amherst, Dallas, Dallas County, TX (US) 75225

( * ) Notice: Subject to any disclaimer, the term of this patent is extended or adjusted under 35 U.S.C. 154(b) by 650 days.

This patent is subject to a terminal disclaimer.

(21) Appl. No.: 10/087,107

(22) Filed: Mar. 1, 2002

(65) Prior Publication Data

US 2002/0081558 A1 Jun. 27, 2002

Related U.S. Application Data

(62) Division of application No. 09/044,487, filed on Mar. 19, 1998, now Pat. No. 6,394,811.

(60) Provisional application No. 60/041,420, filed on Mar. 20, 1997.

(51) Int. Cl.
*G06F 17/00* (2006.01)
*A61B 5/00* (2006.01)
*G06F 7/00* (2006.01)

(52) U.S. Cl. ............... 707/104.1; 707/3; 705/3; 600/300

(58) Field of Classification Search ............. 600/300, 600/301; 705/2, 3; 707/3, 104.1; 706/45; 700/86

See application file for complete search history.

(56) References Cited

U.S. PATENT DOCUMENTS

| | | | |
|---|---|---|---|
| 4,279,258 A | 7/1981 | John | 128/731 |
| 4,527,567 A | 7/1985 | Fischler et al. | 128/419 PT |
| 4,917,117 A | 4/1990 | Brom et al. | 128/782 |
| 4,965,742 A | 10/1990 | Skeirik | 364/513 |
| 5,003,986 A | 4/1991 | Finitzo et al. | 128/731 |
| 5,337,373 A | 8/1994 | Marandici et al. | 382/51 |
| 5,810,728 A | 9/1998 | Kuhn | 600/410 |
| 5,850,836 A | 12/1998 | Steiger et al. | 128/653.1 |
| 5,953,704 A | 9/1999 | McIlroy et al. | 705/2 |
| 6,049,794 A | 4/2000 | Jacobs et al. | 706/45 |
| 6,071,236 A | 6/2000 | Iliff | 600/300 |

*Primary Examiner*—Sam Rimell
(74) *Attorney, Agent, or Firm*—Sidley Austin LLP

(57) ABSTRACT

Software is utilized for allowing a physician to modify the rules of a decision tree so that the individual judgment of the doctor is best utilized. A technician can then carry out tests on a patient, obtain test data in the form of digital data, and apply the test data to the software. The patent test data is then processed through the decision tree to thereby obtain a diagnosis of the patent using the professional judgment without the presence of the physician.

26 Claims, 9 Drawing Sheets

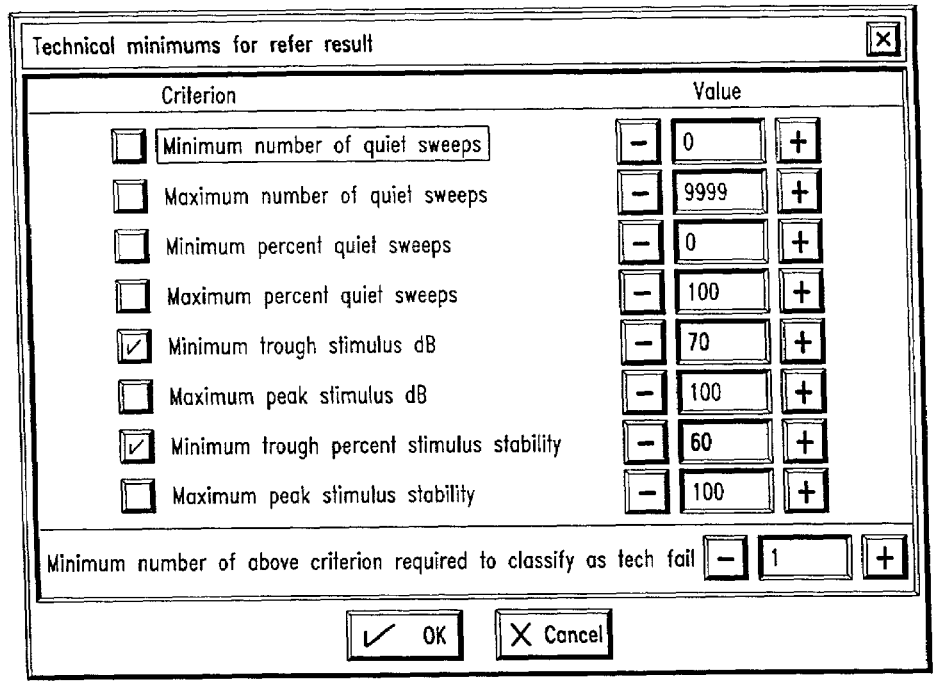

FIG. 10

```
        if((earresult.pass==EAR_PASSED)&&(eardata.wholecorrel<      FIG. 11B
ILO_MINIMUM_WHOLEWAVE_CORRELATION))}earresult.pass =
EAR_REFERRED;strncpy(earresult.failreason,
ILO_INSUFF_WHOLEWAVE_CORREL_STRING,
PAT_RESULT_REASON_FIELD_LENGTH);}
        if((earresult.pass==EAR_PASSED)&&(earcalcs.maxstimdb>
ILO_MAXIMUM_STIM_DB))}earresult.pass=TECH_FAIL;strncpy(earresult.failreason,
ILO_MAX_STIM_TOO_HIGH_STRING, PAT_RESULT_REASON_FIELD_LENGTH);}
        if(earresult.pass==EAR_REFERRED)
        {
                if(earcalcs.minstimdb<ILO_MINIMUM_STIM_DB)}earresult.pass =
TECH_FAIL;strncpy(earresult.failreason, ILO_MIN_STIM_TOO_LOW_STRING,
PAT_RESULT_REASON_FIELD_LENGTH);}
                if(earcalcs.minstimstab<ILO_MINIMUM_STIM_STABILITY)}earresult.pass =
TECH_FAIL;strncpy(earresult.failreason, ILO_STIM_STAB_TOO_LOW_STRING,
PAT_RESULT_REASON_FIELD_LENGTH);}
        }
                if(eardata.nquiet<ILO_MINIMUM_NUM_QUIET)}earresult.pass =
TECH_FAIL;strncpy(earresult.failreason, ILO_INSUFF_NUM_QUIET_STRING,
PAT_RESULT_REASON_FIELD_LENGTH);}
        return earresult.pass;
}
```

FIG. 11A

```
@@@@@@@@@@@@@@@@@@@@@@@@@@@@@@@@@@@@@@@@@@@@@@@@@@@@@@@@
@@@@@@@@@@@@@@@@@@@@@@@@@@@@@@@@@@@@@
int     Eartoae::Newanalysis()
{
        earresult.pass=EAR_REFERRED;
        int     bandcount=0;
        if(eardata.clock_us==ILO_CLOCK_FOR_STANDARD_COLLECTION)//Regular
ILO with bands of 1,2,3,4,5 k
        {
//              if(earcalcs.fft1knet[0]>2.5){bandcount++;}  //This band not used since LF
filter is generally used
                if(earcalcs.fft1knet[1]>ILO_REGULAR_BAND_1_CUTOFF){bandcount++;}
                if(earcalcs.fft1knet[2]>ILO_REGULAR_BAND_2_CUTOFF){bandcount++;}
                if(earcalcs.fft1knet[4]>ILO_REGULAR_BAND_4_CUTOFF){bandcount++;}
                if(earcalcs.fft1knet[3]<ILO_REGULAR_BAND_3_CUTOFF){bandcount = 0;}
                if(bandcount>=ILO_MINIMUM_BANDCOUNT){earresult.pass =
EAR_PASSED;strncpy(earresult.failreason, NULL_STR,
PAT_RESULT_REASON_FIELD_LENGTH);}
                else{strncpy(earresult.failreason, ILO_FAIL_NET_POWER_STRING,
PAT_RESULT_REASON_FIELD_LENGTH);}
        }
        else if (eardata.clock_us==ILO_CLOCK_FOR_QUICK_SCREEN) // which means
QuickScreen w/ bands of 0.8, 1.2, 2.4, 3.2, 4.0 k
        {
//              if(earcalcs.fft1knet[0]>2.5){bandcount++;}  //This band not used since LF
filter is generally used
                if(earcalcs.fft1knet[1]>ILO_QUICK_BAND_1_CUTOFF){bandcount++;}
                if(earcalcs.fft1knet[2]>ILO_QUICK_BAND_2_CUTOFF){bandcount++;}
                if(earcalcs.fft1knet[3]>ILO_QUICK_BAND_3_CUTOFF){bandcount++;}
                if(earcalcs.fft1knet[4]<ILO_QUICK_BAND_4_CUTOFF){bandcount = 0;}
                if(bandcount>=ILO_MINIMUM_BANDCOUNT){earresult.pass =
EAR_PASSED;strncpy(earresult.failreason,NULL_STR,
PAT_RESULT_REASON_FIELD_LENGTH);}
                else{strncpy(earresult.failreason, ILO_FAIL_NET_POWER_STRING,
PAT_RESULT_REASON_FIELD_LENGTH);}
        }
        else    //I don't know what is going on
        {
                earresult.pass=TECH_FAIL;
                strncpy(earresult.failreason,
ILO_UNKNOWN_COLLECTION_PARAM_STRING,
PAT_RESULT_REASON_FIELD_LENGTH);
        }
}
```

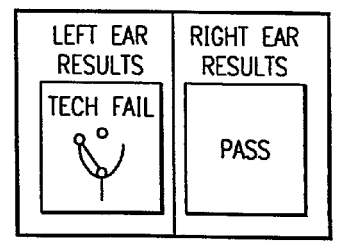

Robert Smith, M.D.
(ADDRESS)

Date of Report: March 17, 1997
Patient:
Date of Birth: March 14, 1997
Case Number:
Mother:
Best Result to Date Right Ear: REFER
Best Result to Date Left Ear: REFER Dear Dr. Smith,
    This child's hearing has been screened using transient evoked otoacoustic emissions or screening auditory brainstem responses. The purpose of the Hearing Screening Program is to facilitate early detection of hearing loss that will be detrimental to the normal development of speech and language.
    The infant has not passed the hearing screening in either ear.
    This is a hearing screen and these results do not mean that the infant has a hearing loss; however, we advise further evaluation before three months of age by an audiologist experienced with auditory brainstem responses and otoacoustic emissions. Normal hearing in at least one ear is critical for speech and language acquisition. Thus, follow-up is essential to determine if this finding is transient or if there is a persistent peripheral hearing loss. Effective early intervention can facilitate language development. This letter superceeds any prior reports. If you have additional questions, please do not hesitate to contact us.

Respectfully,

Richard Jones, Ph.D. CCC/A

FIG. 14

Robert Smith, M.D.
(ADDRESS)

Date of Report: March 19, 1997
Patient:
Date of Birth: March 18, 1997
Case Number:
Mother:
Best Result to Date Right Ear: PASS
Best Result to Date Left Ear: PASS Dear Dr. Smith, This child's hearing has been screened using transient evoked otoacoustic emissions and/or screening auditory brainstem responses. The purpose of the Hearing Screening Program is to facilitate early detection of hearing loss that will be detrimental to the normal development of speech and language.

Screening to date indicates essentially normal peripheral auditory function in both ears. No reevaluation is necessary.

Hearing loss can develop postnatally and these results should not preclude future evaluation if age-appropriate language skills do not develop or if other developmental features, intervening medical events, or parental concern should dictate. Conditions such as congenital infection, or a family history of hearing loss place a child at risk for progressive loss and follow-up evaluations are advised by the Joint Committee on Infant Hearing. This letter superceeds any prior reports. If you have questions concerning the evaluation, please do not hesitate to contact us.

Respectfully,

Richard Jones, Ph.D. CCC/A

FIG. 15

Robert Smith, M.D.
(ADDRESS)

Date of Report: February 28, 1997
Patient:
Date of Birth: February 12, 1997
Case Number:
Mother:
Best Result to Date Right Ear: PASS
Best Result to Date Left Ear: REFER Dear Dr. Smith, This child's hearing has been screened using transient evoked otoacoustic emissions and/or screening auditory brainstem responses. The purpose of the Hearing Screening Program is to facilitate early detection of hearing loss that will be detrimental to the normal development of speech and language.

Screening to date shows essentially normal peripheral auditory function for the right ear. We were unable to obtain an acceptable response for the left ear.

This is a screening test and a unilateral refer does not mean that the infant will have a hearing loss in the left ear. Circumstances including transient middle ear fluid and the test technique itself can produce this result. For immediate confirmation of hearing in the left ear, the infant can be rescreened using auditory brainstem responses or otoacoustic emissions before three months of age. Normal hearing in one ear should allow early speech and language acquisition; however, if developmental features, intervening medical events such as chronic or recurrent otitis media, or parental concern for hearing are present, further evaluation by an audiologist experienced with auditory brainstem responses and otoacoustic emissions is indicated. This letter superceeds any prior reports. If you have additional questions, please do not hesitate to contact us.

Respectfully,

Richard Jones, Ph.D. CCC/A

COMPUTER-AUTOMATED IMPLEMENTATION OF USER-DEFINABLE DECISION RULES FOR MEDICAL DIAGNOSTIC OR SCREENING INTERPRETATIONS

RELATED APPLICATION

This application is a division of application Ser. No. 09/044,487, filed Mar. 19, 1998, which was issued as U.S. Pat. No. 6,394,811 on May 28, 2002, which claims the benefit of U.S. Provisional Application No. 60/041,420, filed Mar. 20, 1997, the entire disclosure of which is incorporated herein by reference.

TECHNICAL FIELD OF THE INVENTION

The present invention relates in general to computer software for providing an analysis of electrical test data, and more particularly to software in which professionals can tailor the processing of the test data according to their choices, thereby allowing a nonprofessional to operate the software and achieve the benefit of the professional's judgment.

BACKGROUND OF THE INVENTION

Many types of diagnoses by physicians and other professionals require specialized interpretations. This often requires the presence and participation of the professional each time a diagnosis is made. In many instances, if the test results of a patient appear to be insufficient to make a diagnosis, the patent must return to the hospital or clinic to be retested. This is time consuming, aggravating and costly to the health care field.

A need therefore exists for a method of allowing a nonprofessional to obtain client data and process the data through software tailored by a professional, thereby obtaining a professional analysis while utilizing the services of a nonprofessional.

SUMMARY OF THE INVENTION

Disclosed is a method and a technique for allowing a nonprofessional to utilize professional-tailored software to carry out an analysis without the professional being present. In the preferred embodiment, a decision tree is provided having multiple levels of analysis, where each level includes plural rules for optional use. Each rule is selectable for use by the professional, and if selected, the rule has provisions for allowing the professional to assign a numerical value for comparison with the client data. In the preferred embodiment, the professional can enter into the levels of the decision tree how many of the selected rules must pass or fail before the level is considered as a pass or fail condition. Also, provisions are made in the software to provide a "refer" output, where the test results are indeterminate and the patient must be tested again while yet present at the test facility.

A nonprofessional can attend to all the patent testing to obtain medical data from the patient—in the form of digital data. The nonprofessional can then apply the digital data test results of the patient to the software decision tree. Since the rules of the software decision tree were tailored by the professional, the output of the software represents a professional analysis that was obtained by a nonprofessional.

BRIEF DESCRIPTION OF THE DRAWINGS

FIGS. 6–10 illustrate the respective five levels of the interpretive tree, and the various rules selectable by the professional in each level;

FIGS. 11A and 11B represent the software code in the utilization of the invention, where the user rules are retrieved and applied to the classification;

FIG. 12 is an example of a results report;

FIGS. 13–15 are exemplary printed reports in the form of letters that provide detailed descriptions of the patient analysis according to the invention.

Figure 1:
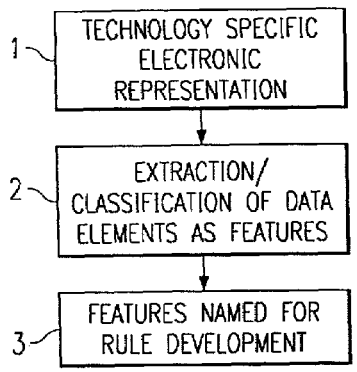
FIG. 1 illustrates the three elements according to the preferred embodiment of the invention.

The purpose of an ever vigilant assistant (EVA software), hereinafter referred to as "EVA," is to leverage the expertise of the professional, be it a physician, audiologist, therapist or scientist, to use and leverage their expertise to provide an interpretation for a technician level person to complete particular tasks. To that end, EVA functions as an interpretive assistant to the professional. For example, EVA is used to provide an automatic interpretation of an auditory brain stem response to evaluate the neurologic status of a patient. EVA can provide an interpretation for an otoacoustic emission to let a technician know whether a particular test conducted on an infant or an adult was a good quality test and what the result was. At this point EVA can be used certainly for specific interpretations of auditory function, but can also be used, for example, in an interpretation of sonograms, of electrocardiograms, of any kind of diagnostic assessment or screening assessment that requires a professional to interpret the test and provide the result. The advantage of EVA is that it allows the individual professional to utilize their own criteria as to what is considered a pass or a fail, or what is a test in which they would want additional information. It is the professional, the physician again, the professional's rules that are applied in EVA. If, for example, there were two different laboratories with two different physicians who had two different views of what was significant in a sonogram of an infant, each of those physicians could utilize EVA to put in his/her own rules so that his own rules would be the ones that applied in the case of their interpretation for a patient. In other words, it is the ever vigilant backup to reduce errors, to be right there—using the physician's expertise at the time the test is done without needing the professional to be present. And again, if two different physicians in two different laboratories in two different places in the country had different interpretive criteria, they can take the technology and apply their own rules so that the laboratory presents their view. This is what EVA embodies.

The input to EVA can be a number of different measures, sonograms, waveforms, it could be waveform morphology interpretation. It could be computerized or electronically generated. It could be specific numbers that are taken from a computer or from a computer generated test. EVA would read the data file, read the absolute values in the data files and extract those values and then look for features that would produce the rules. If one is monitoring a brain function, EVA would pull out the amplitude criteria of the waveform that was generated from the brain, EVA would pull out frequency characteristics. EVA would extract information from a wave emission picked up from an amplifier in the ear canal and it would evaluate features from that emission. Physiologic data from different systems could be assessed. EVA would take the representation and then pull out the key pieces that the professional chose to call important. It is not an interpretation, but it is the expert's view of the test procedure, to leverage his expertise, to allow him or her to do more.

In FIG. 1, the first focus is to establish the features that will be used in defining the rules for evaluating a particular test, diagnostic procedure, or screening measure. In Block 1, the technology specific electronic representation is the first feature that needs to be considered. This might be the specific embodiment of the ILO88, transient otoacoustic emission technology by (OAE) Otodynamics London. The electronic representation might be waveform analysis or might be a waveform drawn from a particular company's EEG equipment. It might take the Grason Stadler GSI60 distortion product otoacoustic emission waveform manufactured by Grason Stadler, and apply the same kinds of rules to that. It could take Bio-Logics distortion product equipment manufactured by Bio-Logics in Mundelein, Ill., and apply a professional's criteria to that electrodiagnostic equipment as well. EVA might take an EKG and pull out data therefrom. The data is taken from the technology (Block 1) and incorporated into a PC based computer running under Windows. In the preferred embodiment, EVA is written in Borland's C++ programming language.

For example, when an OAE test is completed, a probe is placed in an infant's ear and a stimulus is presented to the baby's ear (a sound, a click). An amplifier is attached in the probe assembly picks up the emission from the cochlea of the infant ear, and feeds that back into the computer into the technology specific application where features are displayed. Among the features are the stimulus level, the noise level, the number of quiet and noisy stimuli presented, the background noise level, the amplitude of the various components in the emission, the time of the testing, the frequency of the various components, etc.

These data then reside in the technology specific program completed that has just been run. Based on Block 2 of FIG. 1, there is an extraction or classification of specific data elements as features. This process is described as follows. The data elements are now features selected by the professional and based on his/her judgment. A data element might be the signal-to-noise ratio of the otoacoustic emission at 1600 Hz. Another data element might be the number of quiet sweeps that was presented. All these are elements that could be used in an analysis of the particular test. A data element is a potential feature. There are data elements that might not be used as features by a particular professional because he or she does not consider them to be critical to the analysis. Another professional might use that particular data element. The various features that the professional determines are then identified to develop rules for rule development. This is shown in Block 3. This is the rule development of EVA that is based on the professional's decisions.

The output of EVA after the professional has made his decisions on rule development and after it has been implemented via the C++ programming language, is a decision about the test that was completed on a particular patient. That decision could be that the test was "technically inadequate" and needed to be redone. It could be that the test was a "pass", it could be that the test was a "fail", and that additional testing was needed. It might be that in a particular embodiment, if one looked at cardiac function, no additional testing was needed based on the results of the decision tree rules that were implemented by EVA. A professional might decide to use a morphologic analysis of a waveform to determine if a response was present in the waveform. This might produce the decision that a patient had an abnormal brain stem function. That could be an additional implementation of a rule by EVA.

Figure 2:
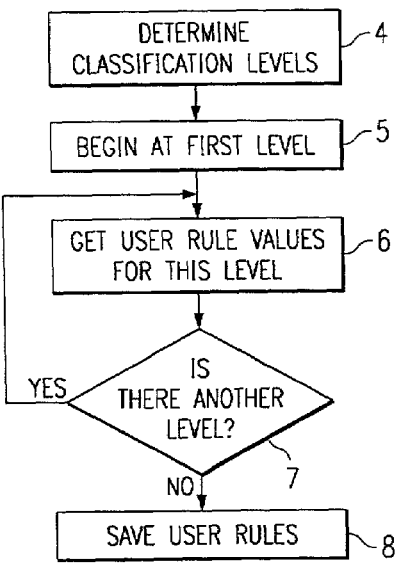
FIG. 2 is a flowchart illustrating the utilization of the user rules of the computer software according to the preferred embodiment.
Figure 5:
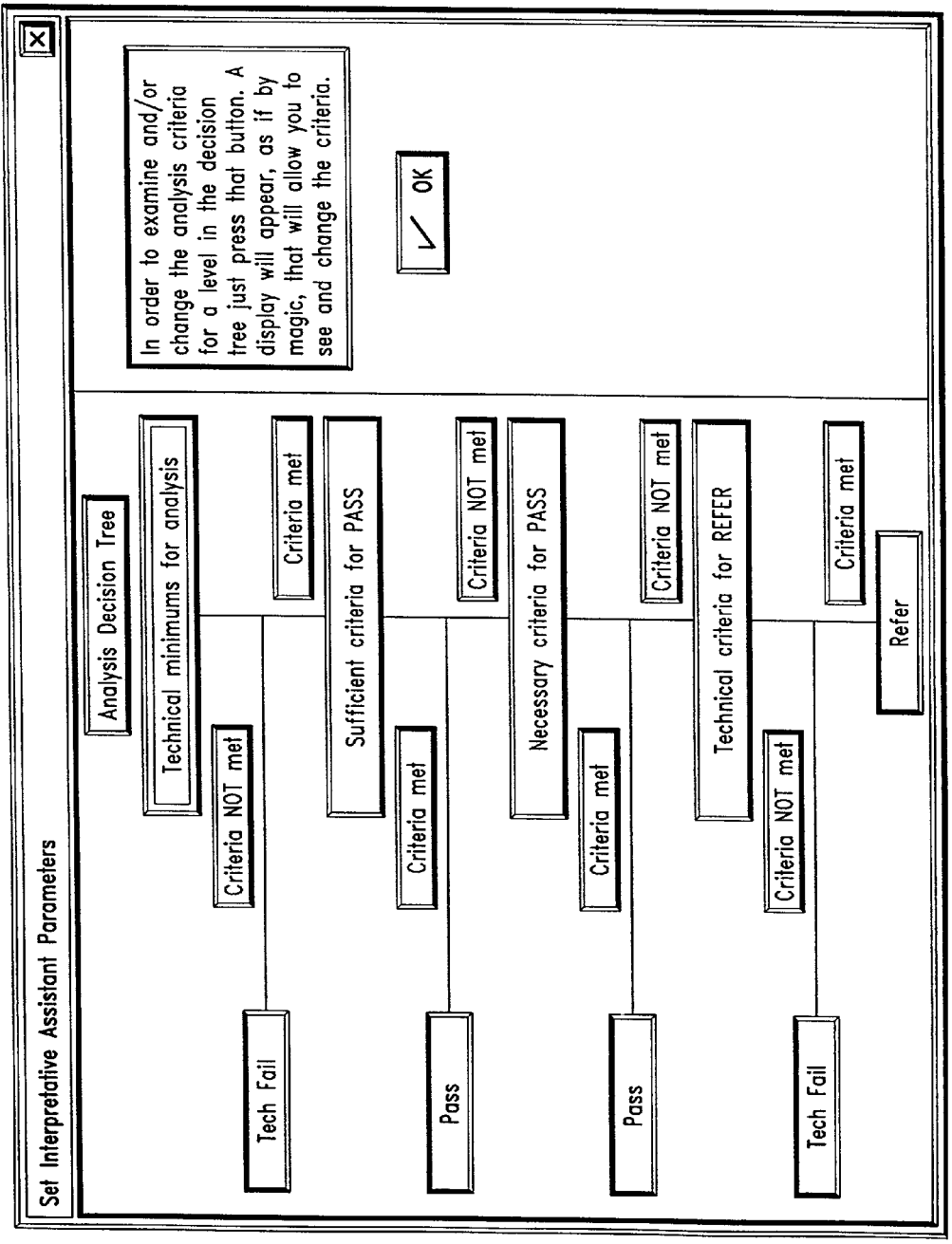
FIG. 5 is a detailed diagram of the analysis decision tree shown generally as Block 4 of FIG. 2.
Figure 7:
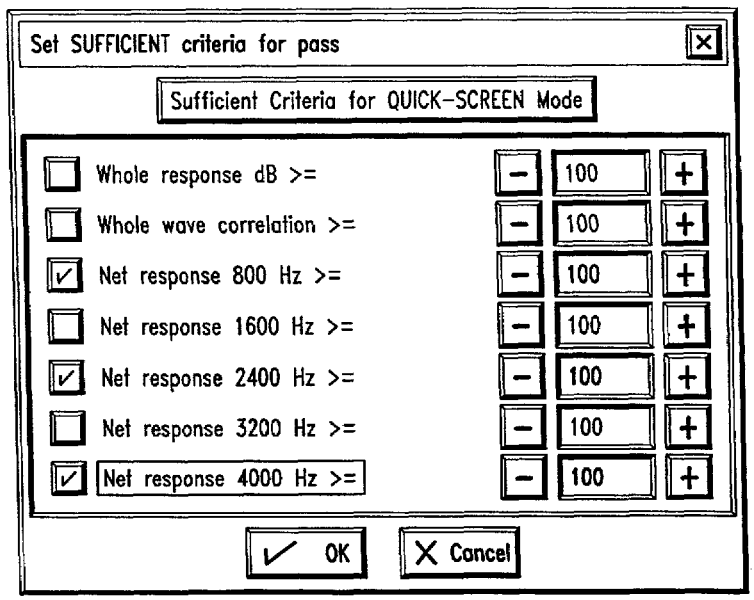
Figure 8:
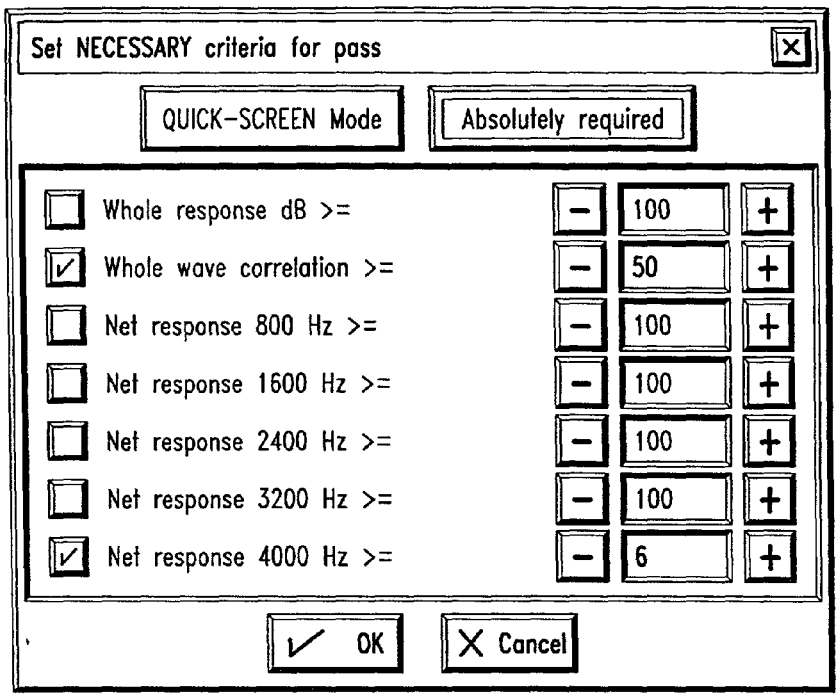

FIG. 2 is a series of Blocks showing the user rule selection. The first block functions to determine classification levels. The embodiment of Block 4 in FIG. 2 is shown in detail in FIG. 5. In the computer screen of FIG. 5, the interpretive assistant parameters for the analysis decision tree are set. It is the analysis decision tree in which the various classification levels are determined. The classification levels are a technical fail level, a pass level, and another technical fail level, and the issues are whether the criteria are met, whether the criteria are sufficient for a pass, necessary for a pass or contributing to a pass. The issue with a technical fail level is whether the technical criteria for "refer" are met or not. Note in FIG. 6 there is a computer screen showing the technical minimums for analysis. In FIG. 7 there is the sufficient criteria shown the criteria sufficient for pass, and this is the specific embodiment for the ILO Otodynamics Transient Evoked Otoacoustic Emission. In FIG. 8 there is shown a computer screen depicting the necessary criteria for pass, and in FIG. 9 there is shown the contributing criteria for a pass level, necessary but contributing. In FIG. 10 there is shown the technical minimums for a refer result. A refer in this case means the patient is sent for additional evaluation. In the right hand corner of FIG. 5, the directions to the professional are shown suggesting how to sub-program EVA and make the decision tree work for that professional. Again, it is the professional's judgments that are being implemented, not generic decisions. It is the professional who is doing the testing, who is responsible for the testing, and who is responsible for the interpretation of the results. The rationale behind EVA is to leverage the expertise of the professional to allow that person to conduct more testing in a high quality and cost efficient manner and to improve patient care through automation.

Referring again to Block 4—Determine Classification Levels—the foregoing illustrates the manner in which this step has been accomplished. The professional would continue at the first level (Block 5). The first level is the first evaluative criteria that the professional has determined will be important in the decision making criteria. This indicates a very hierarchical interpretive assistant. The first level in the specific embodiment is the technical minimum requirement for a test to be analyzed to evaluate it.

Figure 6:
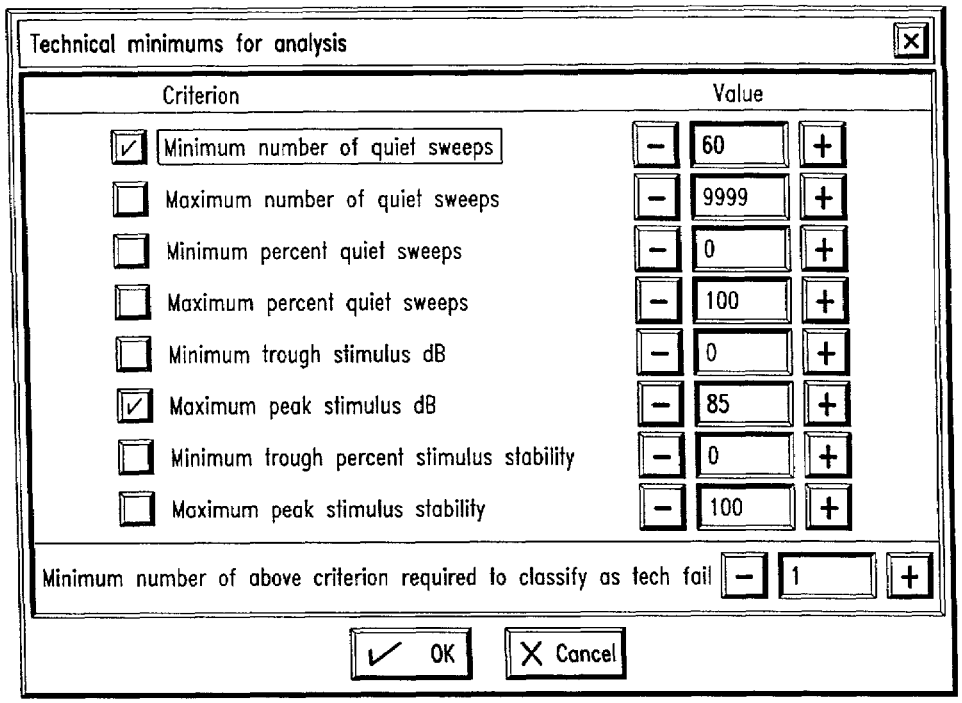

The technical minimums utilized in analysis are shown in FIG. 6. Note that the professional makes judgments and the judgments are related to various criteria that are pulled out and extracted from the particular technology utilized in obtaining data from the patient. It could be the ILO88, it could be the GSI60 Distortion Product, it could be an auditory brain stem response obtained by the by Bio-Logics equipment, it could be the Nicolet auditory brainstem response equipment. It could also be the EMG equipment produced by Nicolet or Bio-Logics. In this case the implementation is the ILO88. The first decision that the professional needs to make is: what is the minimum number of quiet sweeps that must be collected for a test to be analyzed further. The professional can make that decision and increase or decrease the value. In this case, the minimum number of quiet sweeps was set at 60 as the standard. If this were an auditory brain stem response, the minimum number of quiet sweeps might be set at 1000 or 2000 sweeps. The technical minimums for analysis allow the professional to assess other features: the maximum number of quiet sweeps, a percentage of quiet sweeps, minimum and maximum, the lowest stimulus intensity that would be allowed as well as the highest stimulus intensity that would be allowed. Note that the second selected technical minimum for analysis is that the maximum peak stimulus cannot exceed 85 dB. Only two values in this level were selected in the illustrated example: a minimum number of quiet sweeps and a maximum peak stimulus. The user (or the professional) involved had many other choices available. In Block 6 of FIG. 2 the "Rule Values" for this level are obtained. The rule values would be the minimum number of quiet sweeps of 60 and the maximum peak stimulus of 85 dB.

The next query in Block 7 of FIG. 2 is: is there another level to examine? If not, the selected rules are saved and processing continues. If the result of Block 7 is in the affirmative, the user rule values for this level are obtained. In the interpretive assistant parameters of FIG. 5, the next level is to detail the sufficient criteria necessary for a test to be considered a pass for the decision of the professional to make a test, the pass test. This is shown in FIG. 7. The entries of FIG. 7 set the sufficient criteria for a pass. The rules that the professional would make in this case are: what is the whole wave response in dB. What is the whole wave correlation? What is the net response at 800 Hz, at 1600 Hz, at 2400 Hz, at 3200 Hz and at 4000 Hz? Basically, the professional would define his necessary results for the test to be a pass. The selected entries of FIG. 7 are thus the second level that would need to be evaluated by EVA.

The next inquiry in the User Rule Selection of FIG. 2 is: is there another level? If not, EVA saves the rules selected thus far, and then makes the decision based on what has been done. If there is another level, processing goes back and obtains the rules for this level. In this case, there is a necessary criteria for a pass. What is sufficient, what is necessary? The necessary criteria that the professional in this example has made are shown in FIG. 8. There are illustrated seven necessary criteria that have been delineated, and two that are selected by the user as being absolutely required. That is, the whole wave correlation between, in this case, the ILO88 two waveforms that are being collected, must be fifty percent or better. Note also that the signal-to-noise ratio, (net response 4000 Hz), has to be at least 6 dB. That is a requirement for the test to be considered a pass. The question again in Block 7 of FIG. 2 is: is there another level? If not, then EVA saves selected user rules; if yes as shown in Block 8, EVA proceeds to the next level shown in FIG. 9.

The next level is "contributing criteria" for the test to be considered a pass. In the specific embodiment of the ILO88 Quick Screen Transient Otoacoustic Emission test, there is utilized the quick screen testing mode. There are basically another seven criteria that are contributing to a pass. In this example, the professional involved has selected three that contribute. Note that the net response (again, this is signal to noise ratio) at 1600 Hz has to be at least 3 dB, the net response at 2400 Hz has to be at least 3 dB, and the net response at 3200 Hz has to be at least 6 dB. Note also that in terms of contributing criteria, two of those three are required for this to be contributing criteria. The next inquiry is whether there is another level. If not, the rules are saved, if yes, processing returns to look again. In this example, there is one more level to consider, which is shown in FIG. 10.

FIG. 10 is the technical minimum criteria for a professional to decide whether the test is either a refer or a fail. A "refer" means to refer a patient for additional assessment. There are eight criteria that are being examined, i.e., that the user or professional can consider—the minimum number of quiet sweeps, the maximum number of quiet sweeps, etc. Note that in this example the professional has made two decisions, that the minimum stimulus intensity (the trough stimulus) must be no lower than 70 dB, and that the minimum trough percent stimulus stability has to be 60 percent. Either of these two criteria are enough to classify this test as a technical fail. In other words, if the overall stimulus is less than 70 dB, the test is not a fail or a refer, it becomes a technical fail, or a technically inadequate test. Similarly, if the stimulus stability (and that refers specifically to whether the probe in the baby's ear is inserted firmly) is not at least 60, then the test result is interpreted as a technically inadequate test (or a technical fail) rather than a true fail. What that EVA offers the screener, or the tester, or the technician at the bedside is immediate feedback, to "do it over", because it is not a technically acceptable test. This "do it over—it is not technically acceptable" will actually improve patient care because the technician has a chance to correct an error before the patient has left, before money has been spent, and a retest of something that was conducted poorly the first time is necessary. This specific piece of information allows the screener to self correct at a point when it can still impact the quality of care for the patient.

Is there another level? If not, these rules are saved (Block 8 of FIG. 2). The user has made selections on the selected rules, on the decision criteria. The user can be sitting in an office, or setting up EVA to implement his/her decisions. Once the user has completed this step, it is these decisions that will be implemented in the nursery, the laboratory, to wherever the test is going to be performed by whoever is going to perform the test. When the technician begins to conduct a test on a real patient, these are the rules that will be implemented, and the rules that the technician will automatically follow. EVA will provide the technician with immediate feedback as to what the professional wanted. Even if a test is conducted at 2:00 in the morning when the professional is not present, his or her criteria will be implemented consistently and repeatedly. Screener fatigue will not enter, errors won't happen because of inadvertent oversight. The professional's rules are automatically applied day in and day out.

Following the actual testing, whether diagnostic test or screening, the results are displayed for the benefit of the screener. If the results are a pass and a refer, a report is immediately generated and this report contains, again, the words of the professional. In FIGS. 13, 14, and 15, the professional chooses the language. This is another one of the levels that the professional will set up: i.e., report generation. The report will be printed, automatically, at 2:00 in the morning immediately following the test. The test results will be automatically extracted from the technology specific electronic representation, and that information will be placed in the report. So once again the screener cannot make an error and print or otherwise insert an incorrect letter into a patient record. EVA goes in, looks at the test results, makes the decision in real time, and places the results in the letter that will be generated promptly. One more level of potential error in medical care is eliminated by the automatic decision and application of the decision and generation of reports.

Figure 3:
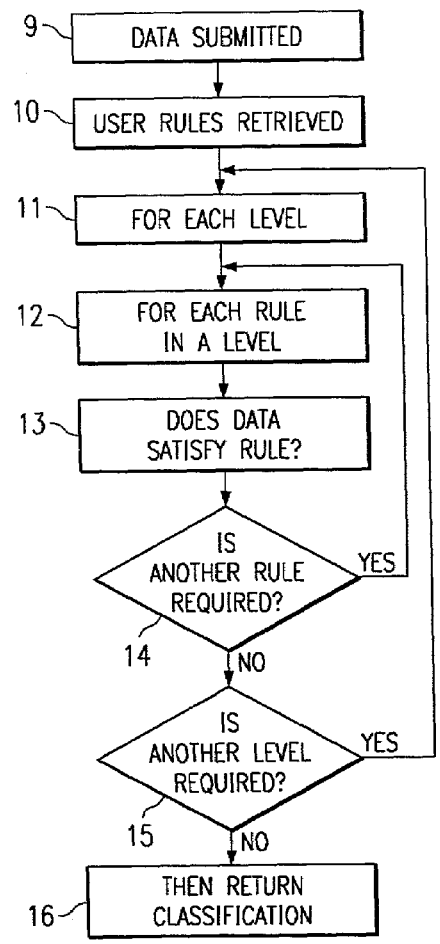
FIG. 3 is a flowchart illustrating the application of the rules established according to the FIG. 2 flowchart.

FIG. 3 is a diagram illustrating the application of the rules. Block 9 in FIG. 3 is "data submitted". This refers to the extraction of data from the electronic technology or electronic representation. Data is submitted (Block 10) and the user rules are retrieved for each level (Block 11). For each rule in a level (Block 12) the question is asked, does the data satisfy the rule (Block 13)? In FIG. 6 there are illustrated technical minimums for analysis. The minimum number of quiet sweeps has been selected as 60. The maximum peak stimulus is less than 85 dB. At this level then, there are two rules in the level. The data obtained from the patient is examined by EVA to see if it satisfies each of these two rules. "Does the data satisfy the rule" is the question posed in Block 13. In FIG. 3 (Block 14), EVA "asks" whether another rule is required? Following a test is completion, the technician retrieves the EVA test result to determine the next steps for a particular patient.

In this example, there are other levels. The sufficient criteria for a pass is shown in FIG. 7. The necessary criteria for a pass is shown in FIG. 8. We note that the whole wave correlation must be 50% according to the selected rules shown in FIG. 8. Note that at 4,000 Hz, the signal of the emission must exceed the noise level of the emission by 6 dB. That is another required rule. If another rule is not required, the next question is: is another level required? Whole wave correlation must be 50%. That's one rule. Is another rule required, yes. The net response must be a 6 dB signal to noise ratio. Within a level, there are these two rules in this example.

Figure 9:
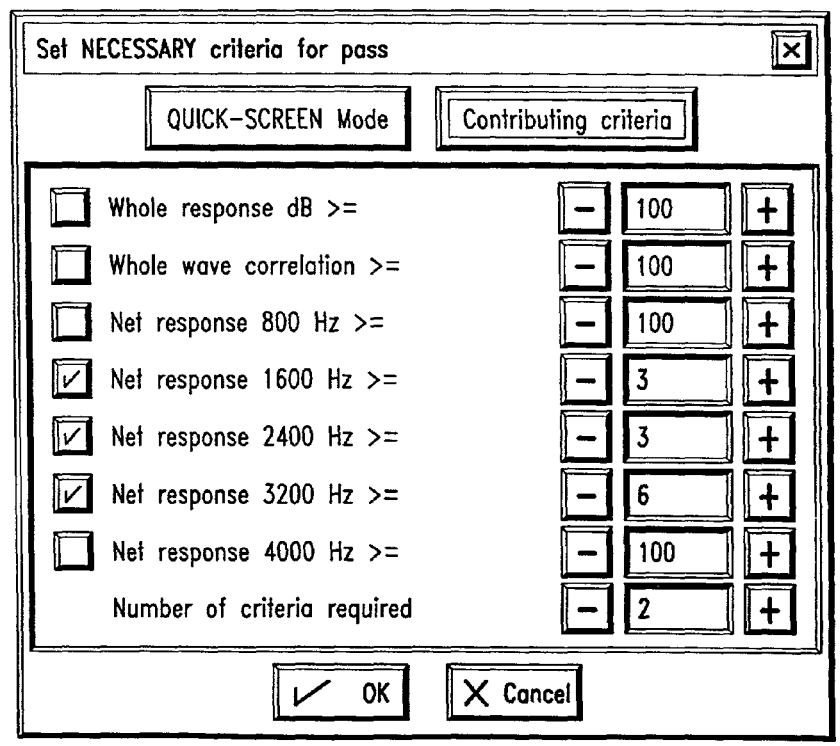

The next question is, is another level required? In this example, there are the contributing criteria for a pass. The answer is yes, another level is required. This is shown in Block 15 FIG. 3. In this example are contributing criteria for pass, and there are three rules out of seven in this level. There are three rules out of seven that the professional has set for contributing criteria (FIG. 9). Only two of those criteria or two of those rules must be implemented or required for the contributing criteria to be met. If a net response or a signal-to-noise ratio at 1600 Hz of 3 dB is met, the 3 dB criteria at 2400 Hz need not be met if the 3200 Hz, 6 dB signal to noise criteria is met.

Is another level required (Block 15)? This is shown in FIG. 10 where there are two technical minimums marked or decided upon by the professional in this example. One minimum is the minimum trough stimulus. The other technical minimum is the percent stimulus stability. Either of these minimums is sufficient to classify the result as the tech fail. It is noted that the minimum criterion required to classify as a tech fail is one. The professional establishing the rules could have changed that number to two if he/she felt it was correct/needed.

Block 16 of FIG. 3 represents the decision. At this point in the processing, all levels and all rules of each level have been assessed. In the example, no more rules are required and no more levels are available to evaluate. EVA returns the classification of the test results based on the professional's interpretive criteria. The classification is considered the result. From the result a report is generated to the referring physician or referring clinician. Classification is pass, fail or refer, or a technically inadequate test. Classification might be refer for additional diagnostic cardiac testing. Classification might be conduct another test. Classification can be basically whatever the professional decides is the next step, based on the rules that he/she is generating. FIG. 12 is an example of a results report. FIGS. 13, 14 and 15 are other example reports. FIG. 13 is a report to a physician showing that the baby in this case born on Mar. 14, 1997, did not pass the test in the right ear or the left ear, that is, the baby "referred" in both ears. The words in the letter are the words that the professional determines to be acceptable. The reports can be modified by another professional. FIG. 14 is an example letter to a physician where the results of the letter are a pass in both the right ear and the left ear on the infant. FIG. 15 shows a test result of pass in the right ear and refer in the left ear. Again, the words of the report are generated by the clinician of record. Note there is no letter for a technically inadequate test, although such a message can be generated. In general, technically inadequate results are required to be conducted again of this example.

Figure 4:
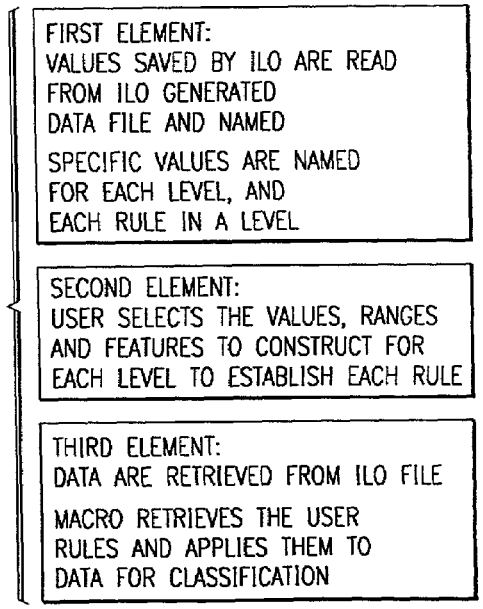
FIG. 4 illustrates the sequence of events for utilization of the invention according to the preferred embodiment.

The specific embodiment of FIG. 4 constitutes three elements. The first element is that the values saved by the ILO88 Otoacoustic emissions equipment (manufactured by Otoacoustic Dynamics) are read from the ILO generated data file. These elements are read and then are named. Specific values are named for each level and for each rule in a level. For the second element, the user selects the values, the ranges and the features. Finally, the data are retrieved from the ILO data file and the macro, the software, i.e., EVA retrieves the user rules and applies them to data for classification. Note then that the software code is the implementation of element 3. The software code can be referred to in FIG. 11, and is the specific embodiment of the third element where the macro retrieves the user rules and applies them to classification.

Through the utilization of the invention patient care is improved because feedback is provided to the technician immediately. The technician can learn immediately from his/her errors and alter the outcome before the patient has left the premises. This can eliminate an inadequate and costly test session.

In summary, this software system operates for the caregiver at the bedside by reducing errors. The software leverages the costly professional's time and energy. It facilitates prompt and accurate patient care through rule governed decision analysis. When widely implemented, it will reduce health costs.

What is claimed is:

1. A method of processing data representing results of a diagnostic or screening test, the method comprising the steps of:
   performing a first procedure to customize decision making criteria, said first procedure including the steps of:
   defining one or more features characteristic of said data;
   defining a plurality of decision levels;
   defining, for each decision level, at least one rule based on at least one of said features; and
   defining, for each rule, a criteria; and
   performing a second procedure to process said data, said second procedure including the steps of:
   receiving said data to be processed, said data having values corresponding to said features;
   comparing said values of said data with said rules according to said criteria; and
   outputting a conclusion based on said comparison, said conclusion comprising an indication of the outcome of the diagnostic or screening test.

2. A method in accordance with claim 1, wherein said first procedure further comprises a step of designating, for each decision level, a quantity of rules effective to influence a result for that level.

3. A method in accordance with claim 1, wherein said first procedure further comprises a step of designating, for each decision level, whether that level represents a condition selected from the group consisting of a technical fail condition, a necessary condition, a sufficient condition, a contributing condition and a refer condition, and wherein said step of comparing said values with said rules according to said criteria includes performing a comparison of said values with said rules according to said criteria for each decision level, and wherein, in said step of outputting a conclusion, the conclusion is output based on a combination of at least a comparison result for said necessary condition and a comparison result for said sufficient condition.

4. A method in accordance with claim 3, wherein, in said step of outputting a conclusion, the conclusion is output based on a combination of at least a comparison result for said necessary condition, a comparison result for said sufficient condition, and a comparison result for said contributing condition.

5. A method in accordance with claim 3, wherein said first procedure further comprises a step of designating, for each decision level, a quantity of rules effective to influence a result for that level.

6. A method in accordance with claim 1, wherein:
said step of comparing said values with said rules according to said criteria includes performing a comparison of said values with said rules according to said criteria for each decision level, and
in said step of outputting a conclusion, the conclusion is output based on a combination of comparison results for at least two levels.

7. A method in accordance with claim 1, wherein said step of comparing said values with said rules according to said criteria includes performing a comparison of said values with said rules according to said criteria for each decision level.

8. A software program including computer executable instructions stored on a computer readable medium, said software program comprising:
a first set of computer code that enables a user to customize decision making criteria, said first set of computer code including:
computer code that enables a user to define features characteristic of a predetermined type of data;
computer code that enables a user to define a plurality of decision levels;
computer code that enables a user to define for each decision level at least one rule based on at least one of said features; and
computer code that enables a user to define for each rule a criteria; and
a second set of computer code that enables the computer to process data, said second set of computer code including:
computer code that receives data of said predetermined type to be processed, said data having values corresponding to said features;
computer code that compares said values with said rules according to said criteria; and
computer code that outputs a conclusion based on said comparison.

9. A software program in accordance with claim 8, wherein said first set of computer code further comprises computer code that enables a user to designate, for each decision level, a quantity of rules effective to influence a result for that level.

10. A software program in accordance with claim 8, wherein said first set of computer code further comprises computer code that enables a user to designate, for each decision level, whether that level represents a condition selected from the group consisting of a technical fail condition, a necessary condition, a sufficient condition, a contributing condition and a refer condition, wherein said computer code that compares said values with said rules according to said criteria performs a comparison of said values with said rules according to said criteria for each decision level, and wherein said computer code that outputs a conclusion does so based on a combination of at least a comparison result for said necessary condition and a comparison result for said sufficient condition.

11. A software program in accordance with claim 10, wherein said computer code that outputs a conclusion does so based on a combination of at least a comparison result for said necessary condition, a comparison result for said sufficient condition, and a comparison result for said contributing condition.

12. A software program in accordance with claim 10, wherein said first set of computer code further comprises computer code that enables a user to designate, for each decision level, a quantity of rules effective to influence a result for that level.

13. A software program in accordance with claim 8, wherein:
said computer code that compares said values with said rules according to said criteria performs a comparison of said values with said rules according to said criteria for each decision level, and
said computer code that outputs a conclusion does so based on a combination of comparison results for at least two levels.

14. A software program in accordance with claim 8, wherein said computer code that compares said values with said rules according to said criteria performs a comparison of said values with said rules according to said criteria for each decision level.

15. A method of analyzing data comprising steps of:
enabling a user to customize decision making criteria by performing steps including:
defining features characteristic of a predetermined type of data representing results of a test;
defining one or more groups of settings, each of said groups of settings including:
a plurality of decision levels;
for each decision level, at least one rule based on at least one of said features; and
for each rule, a criteria; and
storing said groups of settings; and
processing the data by performing steps including:
enabling a user to select a stored group of settings of said stored groups of settings;
receiving data of said predetermined type to be processed, said data having values corresponding to said features;
based on said selected group of settings, comparing said values with said rules according to said criteria; and
outputting a conclusion based on said comparison, said conclusion including an indication of the outcome of the test.

16. A method in accordance with claim 15, wherein said step of enabling a user to customize decision making criteria further comprises a step of designating, for each decision level of each of said groups of settings, a quantity of rules effective to influence a result for that level.

17. A method in accordance with claim 15, wherein said step of enabling a user to customize decision making criteria further comprises a step of designating, for each decision level, whether that level represents a condition selected from the group consisting of a technical fail condition, a necessary condition, a sufficient condition, a contributing condition and a refer condition,
- wherein said step of comparing compares said values with said rules according to said criteria includes performing a comparison of said values with said rules according to said criteria for each decision level, and
- wherein, in said step of outputting a conclusion, the conclusion is output based on a combination of at least a comparison result for said necessary condition and a comparison result for said sufficient condition.

18. A method in accordance with claim 15,
- wherein said step of comparing said values with said rules according to said criteria includes performing a comparison of said values with said rules according to said criteria for each decision level, and
- wherein, in said step of outputting a conclusion, the conclusion is output based on a combination of comparison results for at least two levels.

19. A method in accordance with claim 18, wherein said step of enabling a user to customize decision making criteria further comprises a step of designating, for each decision level, a quantity of rules effective to influence a result for that level.

20. A software program including computer executable instructions stored on a computer readable medium, said program comprising:
- a first set of computer code that enables a user to customize decision making criteria, said first set of computer code including:
  - computer code that enables a user to define features characteristic of a predetermined type of data;
  - computer code that enables a user to define one or more groups of settings, each of said groups of settings including:
    - a plurality of decision levels;
    - for each decision level at least one rule based on at least one of said features; and
    - for each rule a criteria; and
  - computer code that enables a user to store said groups of settings; and
- a second set of computer code that enables a computer to process data, said second set of computer code including:
  - computer code that enables a user to select a stored group of settings of said stored groups of settings;
  - computer code that receives data of said predetermined type to be processed, said data having values corresponding to said features;
  - computer code that, based on said selected group of settings, compares said values with said rules according to said criteria; and
  - computer code that outputs a conclusion based on said comparison.

21. A software program in accordance with claim 20, wherein said first set of computer code further comprises, for each of said groups of settings, computer code that enables a user to designate for each decision level a quantity of rules effective to influence a result for that level.

22. A software program in accordance with claim 20, wherein said first set of computer code further comprises computer code that enables a user to designate, for each decision level, whether that level represents a condition selected from the group consisting of a technical fail condition, a necessary condition, a sufficient condition, a contributing condition and a refer condition,
- wherein said computer code that compares said values with said rules according to said criteria performs a comparison of said values with said rules according to said criteria for each decision level, and
- wherein said computer code that outputs the conclusion does so based on a combination of at least a comparison result for said necessary condition and a comparison result for said sufficient condition.

23. A software program in accordance with claim 20,
- wherein said computer code that compares said values with said rules according to said criteria performs a comparison of said values with said rules according to said criteria for each decision level, and
- wherein said computer code that outputs the conclusion does so based on a combination of comparison results for at least two levels.

24. A software program in accordance with claim 23, wherein said first set of computer code further comprises computer code that enables a user to designate for each decision level, a quantity of rules effective to influence a result for that level.

25. A method in accordance with claim 1, wherein said conclusion further comprises a recommendation based on the outcome of the diagnostic or screening test.

26. A method in accordance with claim 15, wherein said conclusion includes a recommendation based on the outcome of the test.

* * * * *